United States Patent [19]

Heilen et al.

[11] 4,270,006

[45] May 26, 1981

[54] PREPARATION OF ALIPHATIC CARBONYL COMPOUNDS

[75] Inventors: Gerd Heilen, Speyer; Axel Nissen, Leimen; Otto Woerz, Ludwigshafen, all of Fed. Rep. of Germany

[73] Assignee: BASF Aktiengesellschaft, Fed. Rep. of Germany

[21] Appl. No.: 106,884

[22] Filed: Dec. 27, 1979

[51] Int. Cl.$^3$ .................... C07C 45/45; C07C 47/02; C07C 49/04

[52] U.S. Cl. .................................. 568/396; 568/465; 568/462; 568/463; 568/388

[58] Field of Search ............... 568/462, 463, 461, 465, 568/396

[56] References Cited

U.S. PATENT DOCUMENTS

| | | | |
|---|---|---|---|
| 2,485,989 | 10/1949 | Smith et al. | 568/463 |
| 3,953,517 | 4/1976 | Schmitt et al. | 568/462 |
| 4,146,581 | 3/1979 | Nissen et al. | 568/465 |

FOREIGN PATENT DOCUMENTS

| | | | |
|---|---|---|---|
| 1922755 | 8/1972 | Fed. Rep. of Germany | 568/462 |
| 1643044 | 10/1972 | Fed. Rep. of Germany | 568/462 |
| 1014273 | 12/1965 | United Kingdom | 568/462 |
| 1227708 | 4/1971 | United Kingdom | 568/462 |

*Primary Examiner*—Werren B. Lone
*Attorney, Agent, or Firm*—Keil & Witherspoon

[57] ABSTRACT

Aliphatic carbonyl compounds are prepared by an aldol condensation of carbonyl compounds $R^1$—CH$_2$—CO—$R^2$ (I; $R^1$ and $R^2$=H or $C_1$–$C_8$-alkyl) in the presence of hydrogen and of a catalyst which has both condensing and hydrogenating properties, by using a catalyst system wherein the active components are from 1 to 90 percent by weight of a noble metal of group VIII of the periodic table and from 10 to 99 percent by weight of an oxide or salt of a rare earth metal, or of a mixture of different oxides and/or salts of rare earth metals.

1 Claim, No Drawings

PREPARATION OF ALIPHATIC CARBONYL COMPOUNDS

The present invention relates to a novel process for the preparation of aliphatic carbonyl compounds by an aldol condensation of a carbonyl compound of the general formula I $$R^1-CH_2-\underset{\underset{R^2}{|}}{C}=O \qquad I$$

where $R^1$ and $R^2$ are hydrogen or $C_1$-$C_8$-alkyl, under hydrogenating conditions in the presence of hydrogen.

Numerous specific cases of an aldol auto-condensation of an aldehyde or ketone in the presence of hydrogen and of a catalyst system which possesses both condensing and hydrogenating properties have been disclosed.

For example, according to German Published Application DAS No. 1,643,044 methyl isobutyl ketone is obtained from acetone in the presence of hydrogen and of a strongly acidic partially palladium-charged ion exchanger. A similar reaction with different ketones can, according to German Published Application DAS No. 1,922,755, be carried out over a catalyst of Zr phosphate, Hf phosphate, Ti phosphate or Sn phosphate, which additionally contains palladium.

The results achievable by such processes are however only satisfactory in respect of the selectivity with regard to the desired product, but far less satisfactory in respect of the conversion achieved, which can only be increased at the expense of the selectivity.

According to British Pat. No. 1,014,273, aldehydes can be converted in the gas phase, in the presence of hydrogen, to the corresponding dimeric saturated aldehydes over oxidic palladium-containing catalysts such as $Al_2O_3$, MgO, ZnO, $Ca(OH)_2$ and the like; for example, 2-methylpentanal can be obtained from propionaldehyde. However, in spite of the satisfactory selectivity of 73–82%, this process cannot be considered for industrial purposes because of the extremely low space-time yield of 24–34 g of product per hour per liter of reaction space.

The process of U.S. Pat. No. 2,485,989 for the preparation of 2-ethylhexanal from n-butyraldehyde in the presence of hydrogen, a Pd/charcoal catalyst and potassium hydroxide is also unsatisfactory, for technical and economic reasons, since the selectivity of 64% is only moderate and because, after completion of the reaction, a neutralization, i.e. an additional process step entailing additional consumption of materials, is required.

Viewed overall, the processes mentioned have the disadvantage that they are only useful for specific cases, if at all.

German Laid-Open Application DOS No. 2,615,308 has additionally disclosed that a higher ketone of the type $$R'-CH_2-CH_2-\underset{\underset{}{\overset{O}{\|}}}{C}-R''$$

where R' and R" are alkyl, may be prepared by mixed aldol condensation of an aldehyde $$R'-\underset{\underset{}{\overset{O}{\|}}}{C}=O$$

with a methyl alkyl ketone $$CH_3-\underset{\underset{}{\overset{O}{\|}}}{C}-R''$$

by reacting the two components at an elevated temperature in the presence of hydrogen and of a catalyst system which possesses both condensing and hydrogenating properties and contains, as the active constituent, a metal of group VIII of the periodic table and an oxide of a rare earth metal.

As may be seen from the experimental part of the said German Laid-Open Application, both an auto-condensation of the aldehyde and an auto-condensation of the ketone are virtually absent. It had to be concluded from this that the process—at least for industrial purposes—was only suitable for the mixed aldol condensation of an aldehyde with a ketone.

It is an object of the present invention to subject both aldehydes and ketones, under similar conditions, to a hydrogenating aldol condensation with good economics. Such a reaction is commercially particularly important for cases where the products are not required in particularly large amounts. If the products, processes and catalysts are different in every case, different plant is required which, given a limited demand for the products, would remain unused for a large part of the time. If, on the other hand, the plant is appropriately small, it becomes inflexible at times of peak demand and furthermore requires virtually the same amount of labor as a large plant. A process universally applicable to the starting compounds which have been defined would naturally overcome the stated disadvantage.

We have found that an aliphatic carbonyl compound may be obtained economically by an aldol condensation of a carbonyl compound of the general formula I $$R^1-CH_2-\underset{\underset{R^2}{|}}{C}=O \qquad I$$

where $R^1$ and $R^2$ are hydrogen or $C_1$-$C_8$-alkyl, in the presence of hydrogen and of a catalyst which possesses both condensing and hydrogenating properties, if a catalyst system is used wherein the active components are from 1 to 90 percent by weight of a noble metal of group VIII of the periodic table and from 10 to 99 percent by weight of an oxide or salt of a rare earth metal, or of a mixture of different oxides and/or salts of rare earth metals.

Such catalyst systems, which are disclosed in German Laid-Open Application DOS No. 2,615,308 mentioned at the outset, in the main contain palladium, but may also contain platinum, as the noble metal of group VIII of the periodic table. The other noble metals, namely ruthenium, rhodium, iridium and osmium, can mostly also be used, but, for economic reasons, are as a rule less suitable.

Suitable compounds of the rare earth metals (hereafter referred to as RE compounds) are in the main the oxides, especially lanthanum oxide ($La_2O_3$), samarium oxide ($Sm_2O_3$), gadolinium oxide ($G_2O_3$) and holmium oxide (Ho$_2$O$_3$), and especially cerium oxide (Ce$_2$O$_3$), praseodymium oxide (Pr$_2$O$_3$) and neodymium oxide (Nd$_2$O$_3$). If the commercial compound CeO$_2$ is used, it undergoes reduction to Ce$_2$O$_3$ under the reaction conditions.

According to the invention, salts of the rare earth metals may also be used in place of the oxides; for example, the nitrates, sulfates, phosphates, chlorides and carbonates may be used. However, the salts of organic acids, e.g. the acetates, propionates, phenolates, benzenesulfonates and toluenesulfonates, and in particular the salts of higher fatty acids, e.g. of stearic acid, are preferred. If the salts are soluble in the starting compound, they may also be added to the latter before the reaction, so that the mixture then merely has to be passed over a conventional hydrogenating catalyst comprising noble metals of group VIII. This procedure is particularly advisable in cases where the reaction according to the invention is to be carried out over an already existing conventional hydrogenating catalyst, conforming to the definition given, without incurring the expense of a catalyst change. The product finally merely requires distilling from the RE salt.

Furthermore, it is not necessary to use pure RE compounds; instead, their mixtures are equally suitable, for example the commercial technical-grade RE oxides and salts, containing about 90% by weight of an RE oxide or RE salt, the remainder being various other, concomitant RE compounds.

The use of the phrase catalyst system is intended to indicate that it is merely necessary that the two components, namely the noble metal of group VIII and the RE compound, should be present simultaneously during the reaction. Accordingly, the effect desired according to the invention is obtained even when the noble metal and the RE compound are merely present conjointly as a suspension in the carbonyl compound I employed or in an organic solution of I. The situation is similar with a suspension containing a supported catalyst comprising one of the noble metals defined, e.g. Pd on charcoal, and a supported catalyst of an RE oxide, for example an RE oxide supported on alumina.

Such processes are feasible in principle and are frequently suitable for reactions on a relatively small scale or on a semi-commercial scale. However, for continuous industrial operation it is advisable, for well-known technological reasons, to arrange the catalyst as a fixed bed in a reaction tower and to pass hydrogen and the carbonyl compound I, or a solution of I, over this fixed bed.

For the latter purpose, it is preferred to use supported catalysts which carry both the noble metal, e.g. palladium, and RE compound. Such supported catalysts can be prepared by impregnating the carrier with an aqueous solution which contains both a Pd salt, e.g. palladium nitrate, and an RE salt, in the appropriate ratio, drying the impregnated material and heating it in a stream of air, whereupon the RE oxide is formed. The Pd metal then forms automatically under hydrogenating conditions, but it is also possible to subject the supported catalyst to a separate hydrogenation to form the metal. Similar remarks apply to the other noble metals of group VIII.

Examples of suitable carriers are active charcoal, alumina and silica gel in the form of tablets, granules, beads and extrudates with diameters of 2–20 mm and lengths of 2–50 mm.

A loose mass of 1 liter of such a supported catalyst contains about 10–150 g of active catalyst constituents, depending on the geometrical shape and total surface area of the carrier.

In general, the weight ratio of noble metal of group VIII to RE compound is from 1:99 to 90:10, but as a rule catalysts where this ratio is from 5:95 to 80:20 are preferred. Supported catalysts which contain from 2 to 5% by weight of an RE oxide and from 0.2 to 0.5% by weight of palladium, based on the total amount of catalyst, are particularly preferred.

The quantitative or virtually quantitative conversion of 1 mole of the carbonyl compound I in the liquid phase—the preferred embodiment of the process—at 180° C. under a hydrogen pressure of 30 bar requires, depending on the catalyst shape, from about 2 to 10 ml of one of the above supported catalysts, with a reaction time of from about 1 to 10 hours. These are guideline values which vary with the reaction conditions in accordance with known rules, as can readily be established in each case by a few experiments. The reaction conditions are substantially independent of the nature of the carbonyl compound I, so that by means of the process according to the invention it is possible to convert a variety of carbonyl compounds I in one and the same apparatus, without changing the catalyst.

The process proceeds successfully even under atmospheric pressure, but can be carried out under pressures of up to 100 bar to increase the reaction rate. Even higher pressures normally offer no further advantage compared to the technical effort involved. In general, the economically most advantageous results are obtained at pressures of from 1 to 50 bar.

The preferred reaction temperature is from 20° to 250° C., preferably from 20° to 220° C. Below 20° C., the reaction rate drops substantially, whilst above 250° C. limits are increasingly imposed by side-reactions, especially progressive aldol condensations. However, it is noteworthy that even at higher temperatures there is only a slight increase in the hydrogenation of the carbonyl compounds employed, and the carbonyl compounds formed, to give the corresponding alcohols, as long as the hydrogenation of the olefinic double bond, formed as an intermediate stage, is not yet complete. Accordingly, the selective action of the catalysts according to the invention is substantially independent of the temperature, and this is to be regarded as a particular advantage.

If the carbonyl compounds I are liquid under the reaction conditions, the use of a solvent is unnecessary, but can, even in such cases, be an advantage in that it counteracts side-reactions, such as progressive aldol condensations. If the aldehydes are solid, they must be dissolved.

Suitable solvents are all liquids which are inert under the reaction conditions, for example C$_5$–C$_8$-paraffins, cyclohexane, methanol, ethanol, isopropanol, ethyl acetate, toluene and xylene.

The amount of solvent is not critical and is usually from 0.5 to 10 times the amount of the aldehyde.

The reaction according to the invention can be represented as follows:

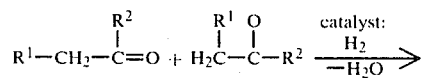

-continued

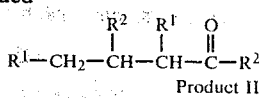
Product II

If $R^2$ is a radical of the type $R^3$—$CH_2$— and $R^3$ is not the same as $R^1$, a mixture of two isomeric carbonyl compounds is obtained as the product II, the proportions in the mixture depending on the reactivity of the two α-$CH_2$ groups.

Industrially particularly important starting compounds I are aldehydes ($R^2$=H), where $R^1$ is hydrogen or branched or, preferably, linear alkyl of 1 to 4 carbon atoms. For example, the following lists starting compounds on the left and products on the right:

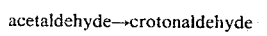
acetaldehyde→crotonaldehyde

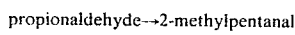
propionaldehyde→2-methylpentanal

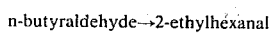
n-butyraldehyde→2-ethylhexanal

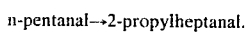
n-pentanal→2-propylheptanal.

Preferred ketones, with a view to the products obtained, are methyl ketones ($R^1$=H), where $R^2$ is alkyl of 1–3 carbon atoms. Since the α-methyl group is more reactive than an α-methylene group, the reaction of mixed ketones I gives substantially only ketones II as the product. For example, the compounds shown on the left give the products shown on the right:

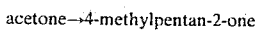
acetone→4-methylpentan-2-one

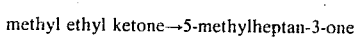
methyl ethyl ketone→5-methylheptan-3-one

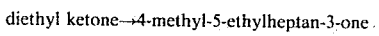
diethyl ketone→4-methyl-5-ethylheptan-3-one

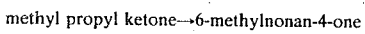
methyl propyl ketone→6-methylnonan-4-one

In other respects, the process according to the invention can be carried out in accordance with the conventional techniques. The same is true of the working up of the reaction mixtures, to give the products.

As is well-known, the products are in some cases important materials per se and in some cases important intermediates for the preparation of, for example, crop protection agents and drugs.

EXAMPLE 1

Preparation of 4-methylpentan-2-one

A tubular reactor of 3 liters capacity and 4.5 cm internal diameter was filled with an irregular packing of 1,800 g of 5–10 mm long and 4 mm thick extrudates of a supported catalyst based on γ-$Al_2O_3$. The catalyst, in which the active composition contained 5 percent by weight of $Pr_2O_3$ and 0.5 percent by weight of Pd, was prepared in a conventional manner by impregnating the γ-$Al_2O_3$ extrudates with an aqueous solution of the catalyst components and then drying and heating the impregnated extrudates in a stream of air. To prepare the impregnating solution, 180 g of 65% strength nitric acid, followed by 85 g of an 11% strength aqueous Pd nitrate solution, were added to a suspension of 100 g of Pr oxide in 75 ml of water. The solution obtained was then made up to 1,840 ml with water. The Pr oxide employed was a commercial mixed oxide of empirical formula $Pr_6O_{11}$.

Per hour, 1.5 liters of acetone were passed by the trickle method, i.e. from above, through this tubular reactor, which was at 150° C. and under a hydrogen pressure of 25 bar. This speed corresponds to a mean residence time of about 2 hours, within which an acetone conversion of 38% was achieved. The yield of 4-methylpentan-2-one, based on material converted, was 91%; in addition, 1% of isopropanol, 3% of the double-sided aldolization product 2,6-dimethylheptan-4-one and 2% of 4-methylpent-3-en-2-one were formed. Since the last-mentioned compound is an intermediate of 4-methylpentan-2-one and can be recycled to the synthesis reaction, in order to undergo hydrogenation, the yield of desired products totalled 92%. The conversion and yields were determined by gas chromatography.

EXAMPLE 2

Preparation of 2-methylpentanal

Using the apparatus described in Example 1, propionaldehyde was converted over 2,100 g of a supported catalyst which consisted of 0.5 percent by weight of Pd and 5 percent by weight of $Pr_2O_3$ on $SiO_2$ as the carrier. The catalyst had the same geometric shape as the catalyst in Example 1, and was prepared by a similar method.

Using a feed of 2.5 liters of propionaldehyde per hour, corresponding to a mean residence time of about 1.2 hours, a propionaldehyde conversion of 38% was achieved at 130° C. under a hydrogen pressure of 25 bar. The yield of 2-methylpentanal, based on the material converted, was 83%. In addition, 3% of propanol, 5% of a mixture of 2,4-dimethylhepta-2,4-dienal and 2,4-dimethylhept-2-enal, 0.5% of 2-methylpentanol and 4% of 2-methylpent-2-enal were formed. Since the last-mentioned compound can, if recycled to the synthesis, also be converted into 2-methylpentanal, the total yield of useful products was 87%.

The conversion and yields were determined by gas chromatography.

EXAMPLE 3

Preparation of 2-methylpentanal

Using the apparatus described in Example 1, propionaldehyde was converted over 1,800 g of a supported catalyst which consisted of 0.5 percent by weight of Pd and 5 percent by weight of $CeO_2$ on γ-$Al_2O_3$ as the carrier. The catalyst had the same geometric shape as the catalyst in Example 1, and was prepared by a similar method.

Using a feed of 3 liters of propionaldehyde per hour, corresponding to a mean residence time of about one hour, a propionaldehyde conversion of 33% was achieved at 170° C. under a hydrogen pressure of 35 bar. The yield of 2-methylpentanal, based on the material converted, was 84%. In addition, 2% of propanol, 6% of the dimethylheptenal mixture mentioned in Example 2, 2% of 2-methylpentanol and 3% of 2-methylpent-2-enal were obtained. As in Example 2, the last-mentioned compound is to be classified amongst useful products, so that the total yield of the latter was 87%.

On increasing the throughput to 3.5 liters/h, the temperature to 200° C. and the hydrogen pressure to 50 bar, 82% conversion was achieved. On the other hand, the yield dropped to 82% (of which 79% was 2-methylpentanal) and 10% of the dimethylheptenal mixture was obtained as a by-product. The amount of the remaining by-products remained virtually unchanged. The analytical data were obtained by gas chromatography,

EXAMPLE 4

Preparation of 2-methylpentanal

In a batchwise experiment, 150 g of propionaldehyde were converted at 180° C. under a hydrogen pressure of 25 bar and with a reaction time of 2 hours over a supported catalyst which contained 0.5 percent by weight of Pd and 5 percent by weight of $Pr_2O_3$ on $\gamma$-$Al_2O_3$ powder as the carrier. The catalyst was prepared by a method similar to that described in Example 1.

The conversion of propionaldehyde was 95% and the yield of 2-methylpentanal and 2-methylpentenal, based on conversion, was 88%. These values were determined by gas chromatography.

EXAMPLE 5

Preparation of 2-methylpentanal

In a batchwise experiment, 150 g of propionaldehyde were converted at 180° C. under a hydrogen pressure of 25 bar and with a reaction time of 4 hours over a supported catalyst which contained 0.2 percent by weight of Pd and 2 percent by weight of $La_2O_3$ on $\gamma$-$Al_2O_3$ powder as the carrier. The catalyst was prepared by a method similar to that described in Example 1. The conversion of propionaldehyde was 91% and the yield of 2-methylpentanal and 2-methylpentenal, based on conversion, was 86%.

These values were determined by gas chromatography.

EXAMPLE 6

Preparation of 2-methylpentanal

In a batchwise experiment, 150 g of propionaldehyde were converted at 180° C. under a hydrogen pressure of 25 bar and with a reaction time of 4 hours, using 2 g of a Pd/active charcoal catalyst which contained 10 percent by weight of Pd and 2 g of neodymium stearate.

The conversion of propionaldehyde was 93% and the yield of 2-methylpentanal and 2-methylpentenal, based on conversion, was 84%. These values were determined by gas chromatography.

EXAMPLE 7

Preparation of 2-ethylhexanal n-Butyraldehyde was converted to the extent of 90% under the conditions of Example 4, but with a reaction time of 3 hours. The yield of 2-ethylhexanal, based on material converted, was 87%. These values were determined by gas chromatography.

EXAMPLE 8

Preparation of 2-(n-propyl)-heptanal n-Pentanal was converted to the extent of 82% under the conditions of Example 4. The yield of 2-(n-propyl)-heptanal and 2-(n-propyl)-hept-2-enal, based on material converted, was 82%. These values were determined by gas chromatography.

We claim:

1. In a process for the preparation of an aliphatic carbonyl compound by aldol condensation of a carbonyl compound of the formula I

where $R^1$ and $R^2$ are hydrogen or $C_1$–$C_8$-alkyl, in the presence of hydrogen and of a catalyst which possesses both condensing and hydrogenating properties, wherein a catalyst system is used wherein, the improvement which comprises: carrying out the process in the presence of an effective amount of a catalyst system wherein the active components are from 1 to 90 percent by weight of a noble metal of group VIII of the periodic table and from 10 to 99 percent by weight of an oxide or salt of a rare earth metal, or of a mixture of different oxides and/or salts of rare earth metals, said catalyst system having both condensing and hydrogenating properties, said process being conducted under pressure of from 1 to 100 bar and at a temperature of from 20° to 250° C.

* * * * *